United States Patent [19]

Querzola et al.

[11] Patent Number: 4,942,250

[45] Date of Patent: Jul. 17, 1990

[54] PROCESS FOR THE PRODUCTION OF CHLOROTHALONYL

[75] Inventors: Giuseppe Querzola, Melegnano; Gino Epis, Lodi, both of Italy

[73] Assignee: S.I.P.C.A.M. - Societa Italiana Prodotti Chimici e per l'Agricoltura Milano S.p.A., Milan, Italy

[21] Appl. No.: 18,948

[22] PCT Filed: Apr. 15, 1986

[86] PCT No.: PCT/EP86/00218

§ 371 Date: Dec. 17, 1986

§ 102(e) Date: Dec. 17, 1986

[87] PCT Pub. No.: WO86/06066

PCT Pub. Date: Oct. 23, 1986

[30] Foreign Application Priority Data

Apr. 17, 1985 [IT] Italy ................................. 20384 A/85

[51] Int. Cl.$^5$ ........................................... C07C 121/56
[52] U.S. Cl. .................................................... 558/411
[58] Field of Search ........................................ 558/411

[56] References Cited

U.S. PATENT DOCUMENTS

| | | | |
|---|---|---|---|
| 3,839,401 | 10/1974 | Lavergne et al. | 558/419 |
| 3,869,494 | 3/1975 | Battershell | 558/308 |
| 4,485,050 | 11/1984 | Casale et al. | 558/419 |

*Primary Examiner*—Mary C. Lee
*Assistant Examiner*—Zinna Northington-Davis
*Attorney, Agent, or Firm*—Sughrue, Mion, Zinn, Macpeak & Seas

[57] ABSTRACT

Process for the production of 2,4,5,6-tetrachloroisophtalonitrile, with formula (I), having a crystallographic structure suited for producing fungicide compositions remaining stable throughout time and having a high biological activity, wherein a thermal and/or mechanical treatment is carried out on the non-suited crystallographic structure, both by gradually decreasing the temperature during the de-sublimation phase, subsequent to industrial synthesis, and by supplying thermal energy—in static or dynamic conditions—and/or mechanical energy to the industrial technical product having a nonsuited crystallographic structure eventually during the phase of preparation or of micronization of said product.

14 Claims, No Drawings

PROCESS FOR THE PRODUCTION OF CHLOROTHALONYL

TECHNICAL FIELD

This invention relates to a process for the production of chlorothalonyl.

BACKGROUND ART

Chlorothalonyl (2,4,5,6-Tetrachloro-isophthalonitrile with formula

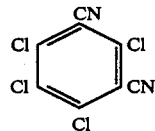

is a fungicide widely used as anticryptogamic in agricultural cultivations and as antifungus for paints of various types.

After carrying out studies, the Applicant has been able to establish the existence of various crystallographyc structures of Chlorothalonyl, showing different physical behaviours and being more or less suited for producing compositions ready for use.

In particular, it has been established that there exists a crystallographyc structure—hereinafter called type I—which, when formed with suitable surface-active and suspending agents as known to the expert in the art, allows one to obtain flowables as well as water wettable powders, having optimal physical characteristics, remaining stable throughout time and having a high biological activity.

The X-ray diffraction spectrogram of said type I crystallographic structure shows some typical bands, as reported in Table 1.

TABLE 1

X-ray diffraction spectrogram of Chlorothalonyl with type I crystallographic structure, in a decreasing order of intensity:

| Diffraction angle (degrees) | Intensity | Interreticular distances (Å) |
|---|---|---|
| 51.2 | 100 | 3.48 |
| 56.0 | 60 | 3.19 |
| 28.8 | 36 | 6.15 |
| 62.3 | 35 | 2.87 |
| 63.6 | 35 | 2.81 |
| 40.1 | 30 | 4.42 |
| 40.7 | 30 | 4.37 |

It has moreover been established that there is another crystallographic structure of Chlorothalonyl—hereinafter called type II—which is not suited, as it is, for producing compositions ready for use; in fact, various tests carried out on compositions including this type of Chlorothalonyl have showed the following:

1. On preparing flowables, the fluid mass undergoes an irreversible hardening, which can take place either after a few hours from preparation, or even after a few months, when the composition, initially deemed suitable for use, has already been delivered to the final users.
2. Whereas, in the case of wettable powder compositions, their capacity to be suspended in water may be greatly reduced, determining the formation of coarse flocculates and giving rise to difficulties of distribution when they are used.

The compositions produced starting from technical Chlorothalonyl with a type II crystallographic structure have also evidenced—parallely to a physical decay—a reduced biological activity in respect of similar compositions produced starting from Chlorothalonyl with a type I crystallographic structure.

The X-ray diffraction spectrogram of the type II crystallographic structure, widely differing from that of the type I structure, is reported in Table 2.

TABLE 2

X-ray diffraction spectrogram of Chlorothalonyl with type II crystallographic structure, in a decreasing order of intensity:

| Diffraction angle (degrees) | Intensity | Interreticular distances (Å) |
|---|---|---|
| 53.3 | 100 | 3.34 |
| 28.8 | 50 | 6.15 |
| 46.8 | 30 | 3.80 |
| 63.2 | 30 | 2.83 |
| 58.1 | 25 | 3.07 |
| 40.8 | 20 | 4.35 |

DISCLOSURE OF THE INVENTION

To eliminate the drawbacks of Chlorothalonyl with a type II crystallographic structure, various production processes have been studied to obtain Chlorothalonyl having a type I structure, namely changing the type II crystallographic structure into a different structure, more suited for producing active compositions which remain stable throughout time.

It has unexpectedly been found that the type II crystallographic structure of Chlorothalonyl can be changed into a different more suitable structure, by supplying an appropriate amount of thermal and/or mechanical energy to said Chlorothalonyl, being distributed over a sufficient period of time.

BEST MODES FOR CARRYING OUT THE INVENTION

In particular, it has been found that, by heating the type II Chlorothalonyl, its crystallographic structure can be changed more quickly into a type I structure if operating while the product is being stirred, or else by simultaneously applying mechanical energy, for instance by forced milling (micronization).

With the product in static conditions, it has been found necessary to heat the type II Chlorothalonyl for at least 8–36 hours at 200°–80° C., while less hours are sufficient, at the aforespecified temperatures, if the type II Chlorothalonyl is kept stirred. On the other hand, if the type II Chlorothalonyl is heated already dispersed in an aqueous phase, and eventually micronized, only a few hours are sufficient at relatively low temperatures (eg. 60°–90° C.), to change said Chlorothalonyl into a different one of more suitable type.

Moreover, it has unexpectedly been found that a Chlorothalonyl of suitable type can be produced directly in the industrial synthesis plant, if care is taken to check that, during the de-sublimation phase, the temperature of Chlorothalonyl decreases gradually, thereby preventing a rapid fall of temperature which would lead to the forming of a type II crystallographic structure, not suitable for producing stable compositions having a high biological activity.

To prevent this drawback already in the phase of industrial synthesis, the processing chambers, starting from the de-sublimation chambers, can be suitably pre-arranged, for instance by supplying proper insulation and/or hot air current and/or adequate mechanical stirring, so as to allow gradual de-sublimation of the Chlorothalonyl, at a temperature lower than the melting temperature (approx. 250° C.) and gradually decreasing over a period of time sufficient to guarantee its crystallization at a suitable energy level (for instance, by keeping the temperature at 250°–80° C. for 4–24 hours).

INDUSTRIAL APPLICABILITY

Thanks to the aforedescribed process, it is possible to produce Chlorothalonyl having a type I crystallographic structure, fit for use in stable compositions which are particularly active as fungicides.

While carrying out the searches, the Applicant has also found that, if the energy level of the heretofore specified thermal and mechanical treatments is not optimal, it could give rise to the production of a Chlorothalonyl with a crystallographic structure defined as type III, namely having a diffraction spectrogram which partly differs from those of the other types, but has at times bands which are typical of the type I or type II Chlorothalonyl.

Table 3 reports the diffraction spectrogram of said type III Chlorothalonyl.

TABLE 3

X-ray diffraction spectrogram of Chlorothalonyl with type III crystallographic structure, intermediate between type I and type II, in a decreasing order of intensity:

| Diffraction angle (degrees) | Intensity | Interreticular distances (Å) |
|---|---|---|
| (A) Typical angles and distances of type III structure | | |
| 53.0 | 100 | 3.36 |
| 28.2 | 40 | 6.28 |
| 61.7 | 30 | 2.90 |
| 47.8 | 20 | 3.72 |
| 67.2 | 20 | 2.67 |
| (B) Typical angles and distances of type I structure (found at times) | | |
| 51.2 | 20 | 3.48 |
| (C) Typical angles and distances of type II structure (found at times) | | |
| 53.3 | 30 | 3.34 |
| 46.8 | 20 | 3.80 |
| 58.1 | 17 | 3.07 |
| 28.8 | 15 | 6.25 |

It has moreover unexpectedly been found that, when use is made—in various compositions—of said Chlorothalonyl with a type III crystallographic structure, having also some diffraction angle and some interreticular distance typical of the type I structure, the mechanical and thermal energy generated during a micronization step both in an aqueous phase (with colloidal mills) or in a dry state (with suitable micronizers)—is sufficient to change the crystallographic structure of Chlorothalonyl from type III into the more suitable type I structure, thereby allowing to produce stable and particularly active compositions. Said phenomenon is above all quite apparent when using Chlorothalonyl with a type III structure for preparing flowables, wherein the wet micronization of the active substance is carried out into a colloidal sand (or pearl) mill, in that the rise in temperature and the kinetic/mechanical energy produced by the friction between the siliceous particles and the solid active substance cause the desired crystallographic transformation, and this is particularly evident especially with a double passage into two colloidal mills placed in direct succession.

We claim:

1. A process for altering the crystallographic structure of 2,4,5,6-tetrachloro-isophthalonitrile produced by chemical synthesis at a temperature above about 250° C., which comprises subjecting the 2,4,5,6-tetrachloro-isophthalonitrile having a crystallographic structure other than that of type I to a at least one of a thermal or mechanical treatment at a temperature lower than about 250° C. for a length of time sufficient to alter the crystallographic structure of said 2,4,5,6-tetrachloro-isophthalonitrile into said type I structure, said type I crystallographic structure, in decreasing order of intensity, being as follows:

| Diffraction angle (degrees) | Intensity | Interreticular distances (Å) |
|---|---|---|
| 51.2 | 100 | 3.48 |
| 56.0 | 60 | 3.19 |
| 28.8 | 35 | 6.15 |
| 62.3 | 35 | 2.87 |
| 63.6 | 35 | 2.81 |
| 40.1 | 30 | 4.42 |
| 40.7 | 30 | 4.37 |

2. Process as in claim 1, wherein the length of the thermal treatment is inversely proportional to the temperature of said treatment.

3. Process as in claim 1, wherein, during the thermal treatment, the 2,4,5,6-tetrachloro-isophthalonitrile is simultaneously subjected to a mechanical stirring treatment.

4. Process as in claim 3, wherein the length of the simultaneous treatment is inversely proportional to the temperature of the thermal treatment and to the strength of the mechanical stirring.

5. Process as in claim 1, wherein, before or during the thermal treatment, the 2,4,5,6-tetrachloro-isophthalonitrile is subjected to a mechanical milling action in order to increase its micronization degree.

6. Process as in claim 5, wherein the length of the treatment is inversely proportional to the micronization degree of the 2,4,5,6-tetrachloro-isophthalonitrile.

7. Process as in claim 1, wherein the thermal treatment is carried out on the 2,4,5,6-tetrachloro-isophthalonitrile immediately after its chemical synthesis and before cooling thereof by gradually decreasing the temperature of the 2,4,5,6-tetrachloro-isophthalonitrile during a de-sublimation phase thereof, to between 250° C. and 80° C. for a length of time varying from 4 to 24 months.

8. Process as in claim 1, wherein the thermal treatment is carried out on cooled 2,4,5,6-tetrachloro-isophthalonitrile, wherein the 2,4,5,6-tetrachloro-isophthalonitrile is heated at a temperature between 200° C. to 80° C. for a length of time varying from 8 to 36 hours.

9. Process as in claim 1, wherein the thermal treatment is carried out on cooled 2,4,5,6-tetrachloro-isophthalonitrile, wherein the 2,4,5,6-tetrachloro-isophthalonitrile is heated at a temperature between 60° C. and 90° C. and simultaneously milled.

10. Process as in claim 9, wherein the milling operation is carried out on two successive mills.

11. Process as in claim 1, wherein the 2,4,5,6-tetrachloro-isophthalonitrile is heated to the desired temperature through the heat developed by a mechanical treatment to which it is subjected.

12. Process as in claim 9, wherein the milling is carried out on the 2,4,5,6-tetrachloro-isophthalonitrile in dry form or in water suspension.

13. Process as in claim 12 wherein an air jet mill or a colloidal pearl mill is used.

14. Process as in claim 1 wherein the 2,4,5,6-tetrachloro-isophthalonitrile comprises at least one of type II and type III crystallographic structure which is converted by the thermal treatment to type I crystallographic structure, said type II crystallographic structure being, in decreasing order of intensity:

| Diffraction angle (degrees) | Intensity | Interreticular distances (Å) |
|---|---|---|
| 53.3 | 100 | 3.34 |
| 28.8 | 50 | 6.15 |
| 46.8 | 30 | 3.80 |
| 63.2 | 30 | 2.83 |
| 58.1 | 25 | 3.07 |
| 40.8 | 20 | 4.35 | and said type III crystallographic structure, being in decreasing order of intensity:

| Diffraction angle (degrees) | Intensity | Interreticular distances (Å) |
|---|---|---|
| (A) Typical angles and distances of type III structure | | |
| 53.0 | 100 | 3.36 |
| 28.2 | 40 | 6.28 |
| 61.7 | 30 | 2.90 |
| 47.8 | 20 | 3.72 |
| 67.2 | 20 | 2.67 |
| (B) Typical angles and distances of type I structure | | |
| | | (found at times) |
| 51.2 | 20 | 3.48 |
| (C) Typical angles and distances of type II structure | | |
| | | (found at times) |
| 53.3 | 30 | 3.34 |
| 46.8 | 20 | 3.80 |
| 58.1 | 17 | 3.07 |
| 28.8 | 15 | 6.25 |

* * * * *